United States Patent
Naparstek (12)

(10) Patent No.: US 6,228,363 B1
(45) Date of Patent: May 8, 2001

(54) PEPTIDES FOR THE TREATMENT OF SYSTEMIC LUPUS ERYTHEMATOSUS

(75) Inventor: Yaakov Naparstek, Jerusalem (IL)

(73) Assignee: Hadasit Medical Research Services & Development Company Ltd., Jerusalem (IL)

( * ) Notice: Subject to any disclaimer, the term of this patent is extended or adjusted under 35 U.S.C. 154(b) by 0 days.

(21) Appl. No.: 09/399,494

(22) Filed: Sep. 20, 1999

Related U.S. Application Data

(63) Continuation of application No. PCT/IB98/00415, filed on Mar. 20, 1998.

(30) Foreign Application Priority Data

Mar. 20, 1997 (IL) .......................................................... 120503

(51) Int. Cl.$^7$ .......................... A61K 39/00; A61K 38/00; A61K 38/04; C07K 16/00; C07K 17/00
(52) U.S. Cl. ........................................ 424/185.1; 530/326
(58) Field of Search ........................... 424/185.1; 530/326

(56) References Cited

FOREIGN PATENT DOCUMENTS

| | | |
|---|---|---|
| 0670495 | 9/1995 | (EP) . |
| 0765660 | 9/1997 | (EP) . |
| 9204914 | 4/1992 | (WO) . |
| 9604926 | 2/1996 | (WO) . |

OTHER PUBLICATIONS

Andria et al., "Diverse $V_H$ and $V_L$ Genes are Used to Produce Anitbodies Against a Defined Protein Epitope" *Journal of Immunology*, vol. 144 (1990), 144(7): 2614–2616 (Exhibit 5).

Ben–Yahuda et al., "The Urine of SLE Patients Contains Antibodies that Bind to the Laminin Component of the Extracellular Matrix." *Journal of Autoimmunity*, vol. 8, No. 2, 1995, pp. 279–291 (Exhibit 6).

Foster et al., "Molecular Analysis of Spontaneous Nephrotropic Anti–Laminin 151(2): Antibodies in an Autoimmune MRL–lpr/lpr Mouse" vol. 151 (1993), J. Immunol 814–824 (Exhibit 7).

Gehlsen et al., "A Synthetic Peptide Derived from the Carboxy Terminus of the Laminin A Chain Represents a Binding Site for the $\alpha_3 B_1$ Integrin" (1992), The Journal of Cell Biology 117(2): 449–459 (Exhibit 8).

Harvath et al. "Laminin Peptides Stimulate Human Neutrophil Motlity " vol. 117 (1994), J. Immunol. 152: 5447–5456 (Exhibit 9).

Lockshin et al. "Lupus Pregnancy—Case–Control Prospective Study Demonstrating Absence of Lupus exacerbation during or after Pregnancy" vol. 77 (1984), The American Journal of Medicine 77: 893–898 (Exhibit 10).

Sabbaga et al. "A Murine Nephritogenic Monoclonal Anti–DNA Autoantibody binds directly to mouse laminin, the major non–collagenous protein component of the glomerular basement membrane"(1989), Eur. J. Immunol. 19: 137–143 (Exhibit 11).

Sasaki et al. "Laminin, a Multidomain Protein" vol. 263 No. 32 (1988), The Journal of Biological Chemistry of 263(32):16536–16544 (Exhibit 12).

Skubitz et al. "Synthetic Peptides form the Carboxyl–terminal Globular Domain of the A Chain of Laminin: Their Ability to Promote Cell Adhesion and Neurite Outgrowth, and Interact with Heparin and the B1 Integrin Subunit"vol. 115 No. 4 (1991), The Journal of Cell Biology 115(4): 1138–1148 (Exhibit 13).

Termaat et al., "Antigen–specificity of Antibodies Bound to Glomeruli of Mice with Systemic Lupus Erythematosus–Like Syndromes" vol. 68 No. 2 (1993), Laboratory Investigation, 68(2): 164–173 (Exhibit 14).

Wilke et al. "Human Keratinocytes Adhere To Multiple Distinct Peptide Sequences of Laminin." (1991), The Journal of Investigative Dermatology, 97(1): 141–146 (Exhibit 15); and.

*Primary Examiner*—Patrick J. Nolan
*Assistant Examiner*—Gerald R. Ewoldt
(74) *Attorney, Agent, or Firm*—John P. White; Cooper & Dunham LLP

(57) ABSTRACT

A method is disclosed for treating systemic lupus erythematosus in a mammalian subject, comprising administering to said subject an effective dose of at least one laminin peptide, or an analog or a derivative thereof. In one exemplary embodiment, the laminin peptide is selected from the group consisting of R38, and claimed R38 analogs and derivatives thereof including 5200, 5104, 5105, 5106, 5107, 5108, 5109, and 5110. The laminin peptides of the present invention may be prepared by known chemical synthetic methods or by biotechnological methods. Assays useful for the diagnosis of and following pathological activity course of systemic lupus erythematosus in patients suffering therefrom.

8 Claims, 7 Drawing Sheets

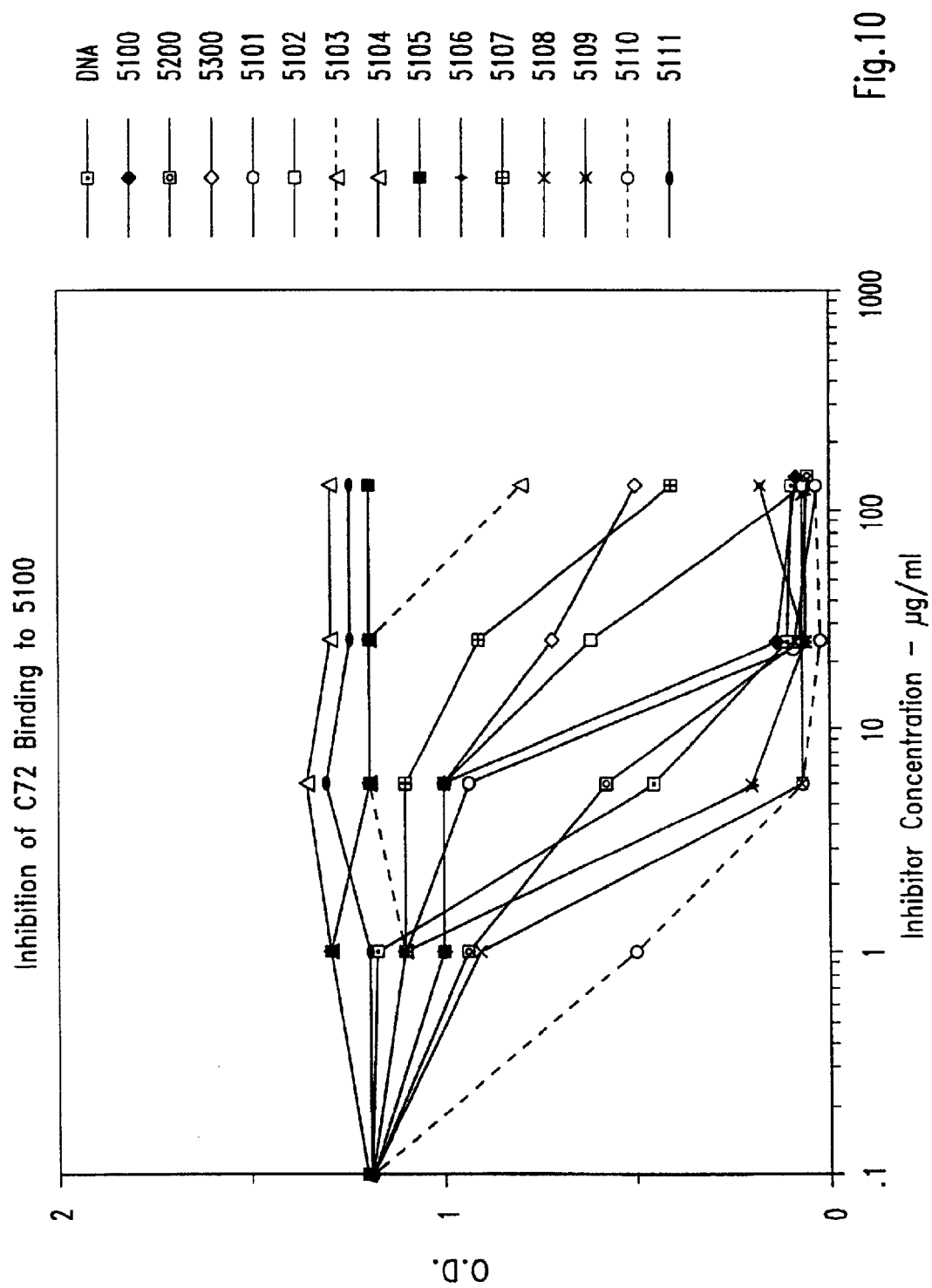

PEPTIDES FOR THE TREATMENT OF SYSTEMIC LUPUS ERYTHEMATOSUS

This application is a continuation of PCT International Application No. PCT/IB98/00415, filed Mar. 20, 1998, designating the United States of America, which claims priority of Israeli Application No. 120503, filed Mar. 20, 1997, the contents of which are incorporated by reference into the present application.

FIELD OF THE INVENTION

This invention relates to the use of laminin peptides and laminin derivatives, including R38 peptide and related analogs for the treatment and detection of systemic lupus erythematosus.

BACKGROUND OF THE INVENTION

Systemic lupus erythematosus (SLE) is an autoimmune disease involving multiple organs. Through the involvement of the kidneys in the autoimmune inflammatory process lupus glomerulonephritis is a major cause of morbidity and mortality in this disease (Alarcon-Segovia D. In: Primer on the Rheumatic diseases. Ed. Schumascher H. R. Arthritis Foundation, Atlanta, Ga., (1988) pp. 96–100).

Serologically, the disease is characterized by the occurrence of a variety of autoantibodies in the serum, of which the most prominent are the anti-DNA auto antibodies (Naparstek Y et al Annu. Rev. Immunol. (1993) 11 79–104). Although low titers of anti-DNA antibodies may occur in various inflammatory and autoimmune diseases, high levels are found mainly in SLE, and the combination of high anti-DNA antibodies with low complement levels is virtually diagnostic of SLE (Wallace D. J. et al In: Dubois' Lupus erythematosus. Lea and Febiger, Philadelphia, 1993).

The binding of immunoglobulins to the glomerular basement membrane (GBM) has been shown by the staining of kidneys derived from lupus patients or lupus strains of mice (Wallace D. J. et al supra). It has also been shown that anti-DNA antibodies eluted from the kidneys of a lupus patient as well as from MRL/1pr/1pr mice cross react with sulfated glycosaminoglycans whereas the serum anti-DNA antibodies do not show this cross reactivity (Naparstek Y et al Arthritis Rheum. (1990) 33, 1554– 1559). These results have suggested that extracellular matrix (ECM) play a role in pathogenesis of lupus as the target for the nephritogenic autoantibodies.

Temmat R. M. et al J. Autoimmun. (1990) 3 531–545, discloses the cross reaction of components of the ECM, like laminin and heparin with murine monoclonal anti-DNA antibodies.

EP Patent Application EP 670,495 discloses the presence of anti-ECM antibodies in the urine of patients with active lupus. Furthermore this patent application discloses the cross reaction of these antibodies with a 200 kDa laminin component of the ECM, and an assay for SLE based on the detection of these anti ECM/laminin antibodies in urine.

R38 is a peptide sequence isolated from the C-terminal region of the mouse laminin α chain (residues 2890–2910 according to Skubitz et al., J. Cell Biol (1991)115 1137–1148, or residues 2851–2871 according to Sasaki M. et al., J. Biol. Chem. (1988) 263, 16,536–16,544). It is located at the junction of the globular domains of the fourth and fifth loops (peptide GD-2 in Skubitz et al. J Cell Biol (1991) 115 1137–1148) and is comprised of the following amino-acid sequence:

KEGYKVRLDLNITLEFRTTSK (SEQ ID NO. 1)

Current SLE therapy is limited to corticosteroids which suppress the over-reactive immune system. This therapy is not specific and its inevitable side effects may themselves be fatal. Furthermore, immunosuppressive therapy is complicated and its initiation is based on a combination of clinical symptoms, blood serological tests and kidney biopsy. There is therefore a need for a more specific therapy for SLE that will not be associated with the side effects of the immunosuppresive agents as well as a more specific and less invasive assay for the evaluation of disease activity. Indeed a recent review (The Lancet (1995) 310 1257–1261) stated that blood tests though useful in confirming diagnosis of SLE are "less useful in monitoring disease activity."

None of the above mentioned references disclose the treatment of systemic lupus erythematosus by the administration of the R38 peptide or analogs thereof. Moreover none of the above mentioned references disclose the use of R38 peptide in a diagnostic test for the disease or in monitoring disease activity. The contents of all these patents and all literature references referred to above are hereby incorporated by reference in their entirety.

SUMMARY OF THE INVENTION

It is therefore an object of the present invention to provide a method for treating systemic lupus erythematosus comprising the administration of laminin peptides.

Another object of the present invention is to disclose R38' and other novel analogs and derivatives of R38 peptide, the administration of which comprises a method for treating systemic lupus erythematosus.

A further object of the present invention is to provide a diagnostic test for the disease by using the R38 peptide, R38' peptide and other structurally related analogs and derivatives thereof.

The invention also relates to pharmaceutical compositions comprising R38 peptide, R38' peptide and other novel analogs and derivatives of R38 peptide, or pharmaceutically acceptable salts thereof for use in the treatment of SLE.

As used herein the term "R38 peptide" is used to include the R38 peptide itself, analogs, derivative and fragments thereof that retain the activity of the complex peptide. The term analogs is intended to include variants on the peptide molecule brought about by, for example, homologous substitution of individual or several amino acid residues. The term derivative is used to include minor chemical changes that may be made to R38 itself or analogs thereof that maintain the biological activity of R38 and similarly the term "fragments" is used to include shortened molecules of R38.

BRIEF DESCRIPTION OF THE FIGURES

FIG. 10 shows the inhibition of C72 binding to R38 (5100) by DNA and by R38 analogs.

DESCRIPTION OF THE PREFERRED EMBODIMENTS

Figure 1:
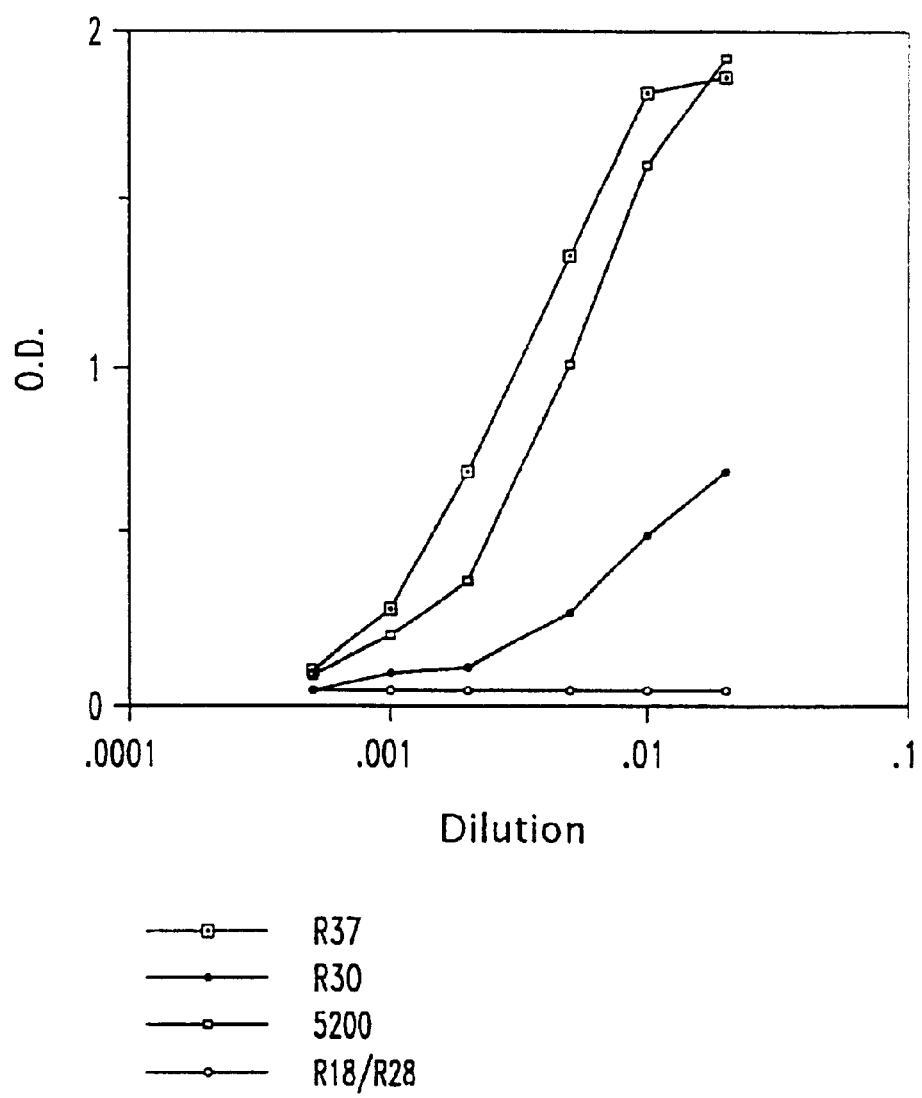
FIG. 1 shows the direct bonding of C72 murine anti-DNA antibody to laminin peptides.

Accordingly the present invention relates to the use of laminin peptides for the treatment of systemic lupus erythematosus.

The present invention is based on the observation that R38 peptide, which is a peptide derived from the C-terminal region of the mouse laminin α chain, is recognized by pathogenic lupus antibodies and may therefore possess therapeutic potential in the treatment of systemic lupus erythematosus by competing with the binding to the lupus antibodies.

Furthermore the present invention relates to the use of a mixture of at least two or more different peptides derived from laminin for the treatment of systemic lupus erythematosus. In a preferred embodiment, at least one of the peptides is R38 or an analog thereof.

The invention also relates to a method of monitoring disease activity of patients suffering from SLE comprising detecting the ability of the antibodies in the urine to bind to the R38 component of the laminin. This binding can have a direct correlation to disease activity evaluated by a combination of various laboratory parameters.

An increase in the amount of antibodies binding to R38 may indicate an approaching active phase of the disease and a declining level of antibodies, an approaching remission. Therefore, this method provides an assay for detecting changes in the level of laminin-specific antibodies and many enable the initiation of therapy prior to the onset of an active phase of the disease.

This method also provides an easy assay that can be used by the patients themselves as it is performed using urine and does not require venipuncture. It may be used as a diagnostic assay, a routine assay for evaluation of disease activity, for early identification of disease exacerbation and for early therapeutic intervention in lupus nephritis.

The R38 peptide or analogs, fragment or derivatives thereof may be used in such an assay using the methods described in EP 670,495. Thus, the R38 peptide may be bound to a solid phase and incubated with the urine from a patient. If the patient is suspected of suffering from SLE, suffering from SLE or is approaching an active phase of the disease, the level of R38-binding antibodies in the urine will increase.

Detection of R38-binding antibodies may be undertaken by any method known by one skilled in the art. Examples of such methods of detection include ELISA and variations thereon, chemiluminescent techniques, etc. The actual method of detection is not crucial to the success of the assay. The level of R38-binding antibodies observed may then be compared to values observed in a control group. The control group may consist of healthy volunteers, or the patient may act as an internal control i.e. the observed value is compared to an earlier value from the same patient. In this manner a profile of the patient's disease state may be compiled and used as an indicator of further active phases or remission states of the disease.

Pharmaceutically acceptable salts of the R38 peptide include both salts of the carboxy groups and the acid addition salts of the amino groups of the peptide molecule. Salts of the carboxy groups may be formed by methods known in the art and include inorganic salts such as sodium, calcium, ammonium, ferric or zinc salts and the like and salts with organic bases such as those formed with amines such as triethanolamine, arginine or lysine, piperidine, procaine and the like. Acid addition salts include salts with mineral acids such as hydrochloric acid and sulphuric acid and salts of organic acids such as acetic acid or oxalic acid.

The pharmaceutical composition may contain laminin peptides such as the R38 peptide as unique peptides or in polymerized or conjugated forms attached to macromolecular carriers or polymers. The compositions may optionally contain pharmaceutically acceptable excipients. In an alternative embodiment the composition may contain the R38 peptide alone.

The route of administration may include oral, intravenous, intra-peritoneal, intra-muscular, subcutaneous, intra-articular, intra-nasal, intra-thecal, intra-dermal, trans-dermal or by inhalation.

An effective dose of the R38 peptide for use in treating SLE may be from about 1 μg to 100 mg/kg body weight, per single administration, which may be easily determined by one skilled in the art. The dosage may depend upon the age, sex, health and weight of the recipient, kind of concurrent therapy, if any, and frequency of treatment.

EXAMPLES

GENERAL

The Peptides

Peptides R26, R28, R30, R31, R35, R37, and R38 (also referred hereinafter as "5100") derived from the C-terminal of mouse laminin α chain, and the R18 peptide derived from the N-terminal of mouse laminin α chain were tested. The peptides are 17–22-mer synthetic peptides, and were prepared by the F-moc technique (Carpino L A & Han G Y (1972) J Org Chem 37 3404). These peptides could also be produced by methods well known to one skilled in the art of biotechnology. For example, using a nucleic acid selected from the group including DNA, RNA, cDNA, genomic, synthetic DNA, mRNA, total RNA, hnRNA, synthetic RNA, the desired peptides may be produced in live cell cultures and harvested.

The sequence of the peptides is presented in the Table 1:

TABLE 1

Laminin Derived Peptides.

| PEPTIDES | RESIDUES (*) | SEQUENCE |
| --- | --- | --- |
| R18 | 42–63 | RPVRHAQCRVCDGNSTNPRERH (SEQ ID NO. 2) |
| R26 | 2443–2463 | KNLEISRSTFDLLRNSYGVRK (SEQ ID NO. 3) |
| R35 | 2547–2565 | TSLRKALLHAPTGSYSDGQ (SEQ ID NO. 4) |
| R37 | 2615–2631 | KATPMLKMRTSFHGCIK (SEQ ID NO. 5) |
| R28 | 2779–2795 | DGKWHTVKTEYIKRKAF (SEQ ID NO. 6) |
| R38 | 2890–2910 | KEGYKVRLDLNITLEFRTTSK (SEQ ID NO. 7) |
| R30 | 3011–3032 | KONCLSSRASFRGCVRNLRLSR (SEQ ID NO. 8) |

(*) Residue designations per Skubitz supra.

Other laminin peptides used for comparative purposes in the Examples include AS31 (comprising the residue YIGSR), AC15 and F9 (other laminin peptides) and R27 a peptide from the 4th loop of the globular region of the laminin α chain.

Additional peptides which are fragments of, or analogs closely derived from R38 have been constructed and are presented in Table 2 hereinbelow. Peptides 5200 and 5101–5111 disclosed in Table 2 were prepared in the same manner as the peptide of Table 1 hereinabove. The Table 2 peptides comprise R38 (5100), human R38 (5300), fragments of R38, a fragment 5111 derived from 5300 or analogs of R38 wherein one or more point substitutions were made according to techniques which are well known to one skilled in the art. These peptides were constructed to investigate, among other things, the effect on anti-DNA antibody binding activity caused by changing the net charge of the R38 peptide.

Anti-Peptide (Direct Binding) ELISA:

Wells were coated with 10 μg/ml of the peptides, blocked with 1% BSA (bovine serum albumin) in PBS (pH 7,4), reacted with appropriately diluted serum or urine samples or monoclonal antibodies, incubated with anti-human or anti-mouse immunoglobulin enzyme conjugated to alkaline phosphatase and detected by addition of substrate (Sigma 100 Phosphatase Substrate Tablets) and color development using an Organon Teknika Microwell System spectrometer at wavelength of 405 nm.

Competitive Inhibition Assays:

In competitive inhibition assays, the antibodies were incubated with various concentrations of the inhibitor (for example: peptide, DNA, heparin) or with DNase for 45 minutes at room temperature and the remaining binding was then evaluated by ELISA as described heretofore.

TABLE 2

Synthetic Peptides Analogous To Mouse R38 Peptide

| Peptide # | AMINO ACID SEQUENCE | DESCRIPTION | Net Charge |
|---|---|---|---|
| 5100 | KEGYKVRLDLNITLEFRTTSK (SEQ ID NO. 9) | Mouse R38 | +2 |
| 5200 | KEGYKVRLDLNTTLEFRTTSK (SEQ ID NO. 10) | Mouse R38 analog | +2 |
| 5300 | KEGYKVQSDVNITLEFRTSSQ (SEQ ID NO. 11) | Human R38 | 0 |
| 5101 | KEGYKVRLDLNITLEF (SEQ ID NO. 12) | Res. 1–16 of 5100 | 0 |
| 5102 | VRLDLNITLEFR (SEQ ID NO. 13) | Res. 6–17 of 5100 | 0 |
| 5103 | LDLNITEFRTTSK (SEQ ID NO. 14) | Res. 8–21 of 5100 | 0 |
| 5104 | AEGYAVALDLNITLEFATTSA (SEQ ID NO. 15) | Ala subst. of 5100 at all positive a.a | −3 |
| 5105 | KEGYKVELDLNITLEFETTSK (SEQ ID NO. 16) | charge subst. to neg. at 5100 a.a. 7 and 17 | −2 |
| 5106 | KEGYKVELDLNITLEFRTTSK (SEQ ID NO. 17) | charge subst. to neg. at 5100 a.a. 7 | 0 |
| 5107 | KEGYKVRLDLNITLEFETTSK (SEQ ID NO. 18) | charge subst. to neg. at 5100 a.a. 17 | 0 |
| 5108 | KAGYKVRLALNITLAFRTTSK (SEQ ID NO. 19) | Ala subst. of 5100 at all negative a.a. | +5 |
| 5109 | KEGYKVRLALNITLEFRTTSK (SEQ ID NO. 20) | Ala subst. of 5100 a.a. 9 | +3 |
| 5110 | KEGYKVRLDLNITLAFRTTSK (SEQ ID NO. 21) | Ala subst. of 5100 a.a. 15 | +3 |
| 5111 | VQSDVNITLEFR (SEQ ID NO. 22) | Res. 6–17 of 5300 | −1 | a.a. Amino Acid

Monoclonal Antibodies

The C72 murine anti-DNA antibody has been derived from (NZBxNZW)F1 lupus mice by the hybridoma technique as described in Eilat D. et al J. Immunol. (1991) 147 361–368. The monoclonal anti-DNA antibodies DIL6 and B3 were derived from lupus patients by hybridoma technique as described in Ehrenstein M. R. et al J. Clin. Invest. (1994) 93 1787–1799 and Ehrenstein M. R. et al Kidney Inter. (1995) 48 705–711.

It should be understood that the following description contemplates use of antibodies specific to the laminins and to the peptides disclosed herein. Methods for producing peptides specific to the laminin peptides and to R38 and its analogs and derivatives are well known to one skilled in the art. In this regard, specific reference may be had to the test "Antibodies, A Laboratory Manual," Ed Harlow and David Lane, Cold Spring Harbor Publishing, 1988, the contents of which are incorporated herein by reference. This reference discloses methods which may be used for obtaining mono-specific antibodies, i.e., monoclonal antibodies and polyclonal antibodies directed against laminin peptides.

% inhibition was computed as

O.D. binding without inhibitor−O.D. binding with inhibitor× 100=% inhibition O.D. binding without inhibitor

EXAMPLE 1: BINDING OF LAMININ PEPTIDES TO SLE ANTIBODIES

A: Murine SLE antibodies bind to C terminal peptides of laminin α chain

The interaction of the C72 murine anti-DNA antibody with laminin peptides was analyzed by ELISA as described above. The C72 conditioned medium was diluted in PBS in various dilutions. The results are summarized in FIG. 1 which shows the binding of C72 murine anti-DNA antibody to the 5200, R37, and R30 peptides, but not to R28 or R18 peptides of the laminin α chain. Control murine antibody, the anti-HEL, Hy5 did not bind to the 5200 peptide (data not shown).

B: Inhibition of the binding of C72 to 5200 is inhibited by DNA and Heparin

Figure 2:
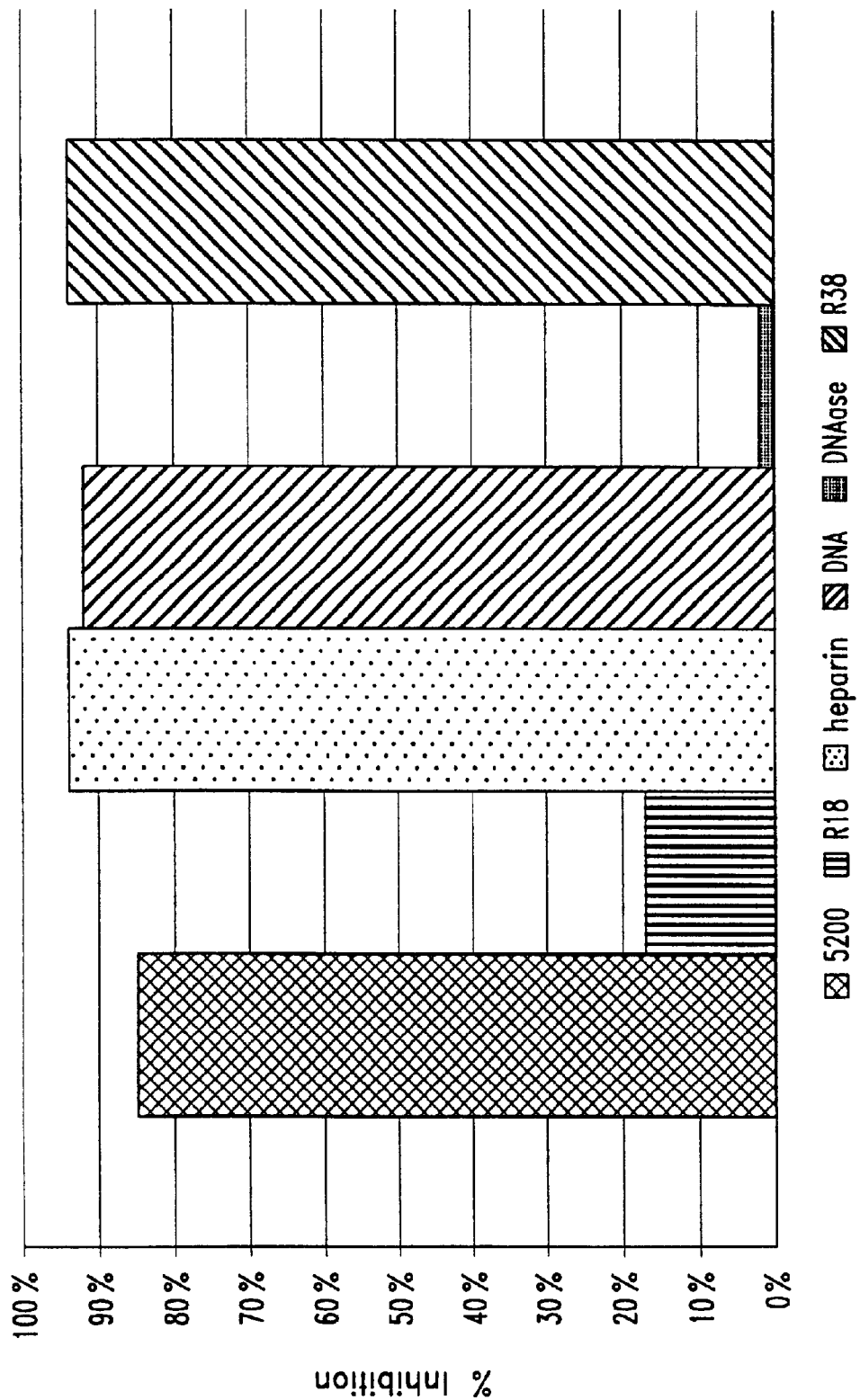
FIG. 2 shows the inhibition by R38, 5200, DNA, DNase and heparin of the binding of C72 to the R38 analog 5200 (sometimes referred to herein as R38')

The binding of C72 to 5200 was tested before and after incubation with 5200, R38, R18, Heparin, DNA and DNase. The results are summarized in FIG. 2 which shows the inhibition of the binding of C72 to 5200 by the R38 or 5200 peptides of the present invention, by DNA and by heparin, but not by a control peptide or treatment with DNase. The percent inhibition is the percent reduction of the O.D. after incubation with the inhibiting agent.

EXAMPLE 2: POLYCLONAL MURINE ANTIBODIES BIND TO THE 5200 PEPTIDE

Analysis of the interaction of MRL/1pr/1pr urine antibodies with the 5200 peptide by a direct binding ELISA revealed specific binding. Thus, pooled urine from at least 5 mice (either MRL/1pr/1pr or control mice, e.g. BALB/c) was added to wells coated with R38' (5200), R18 or DNA as described above and bound 5200 assayed by ELISA.

Binding of Murine Urinary Immunoglobulins To 5200

Each group is comprised of pooled urine.

| MICE | ANTIGEN | | |
|---|---|---|---|
| | DNA | 5200 | R18 |
| BALB/c | U.D. | U.D. | U.D. |
| MRL/lpr/lpr | U.D. | 0.26(*) | U.D. |

U.D.—Undetected
(*)O.D. at 405 nm.

U.D.—Undetected (*) O.D. at 405 nm.

EXAMPLE 3: HUMAN MONOCLONAL LUPUS ANTIBODIES BIND THE 5200 PEPTIDE

Figure 3:
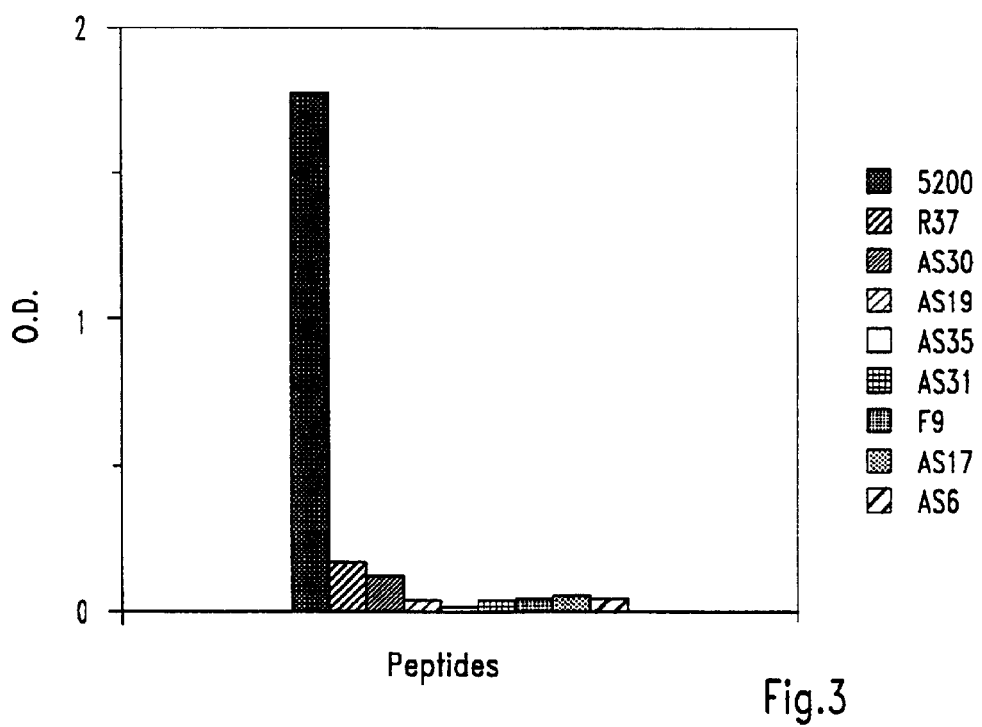
FIGS. 3 and 4 show the binding of the human lupus monoclonal anti-DNA antibodies (DIL6 and B3) to laminin peptides and derivatives thereof.
Figure 4:
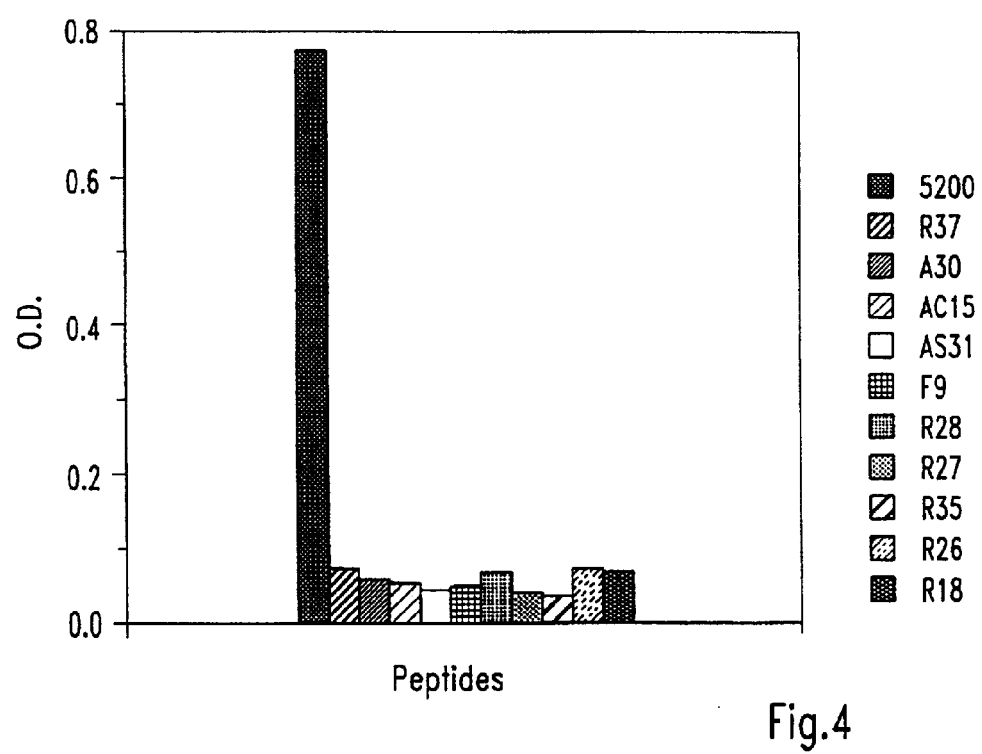

The human monoclonal anti-DNA antibodies DIL 6 and B3 were derived from lupus patients by the hybridoma technique. As shown in FIGS. 3 and 4 these antibodies were found to bind to the 5200 peptide but not to other laminin peptides tested. In FIGS. 3 and 4, the peptides are referred to as denoted above or as follows; AS30 is R27, AS19 is R35, AS35 is R26, AS17 is R28 and AS6 is R18.

EXAMPLE 4: EFFECT OF R38 (5100) & R38' ON THE CLINICAL COURSE OF MURINE SLE

To test whether R38 peptides can affect the course of SLE we have tested their effect on MRL/1pr/1pr mice disease. 60 μg of 5200 (R38' alone or in peptide combinations, 30 μg of each) in 0.1 ml PBS, was injected i.p. to 6 week old female MRL/1pr/1pr mice once a week for 16 weeks and the mice were evaluated for survival (FIG. 8), and for renal histology.

50 μg of 5100 (R38) or 5300 (human R38) in 0.1 ml PBS, was injected i.p. to 6 week old MRL/1pr/1pr mice three times a week and the mice were evaluated for survival (FIG. 9), and for renal histology. Control mice received 0.1 ml phosphate buffer solution. Each test and control group contained 12–15 mice.

Figure 8:
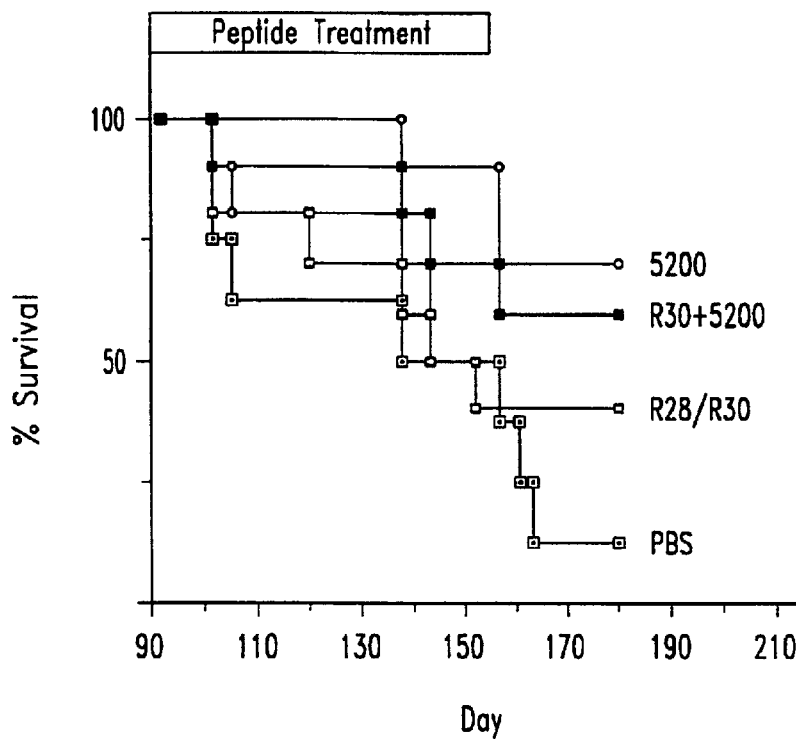
FIG. 8 shows the effect of 5200 (R38') treatment on prolongation of survival of lupus mice.
Figure 9:
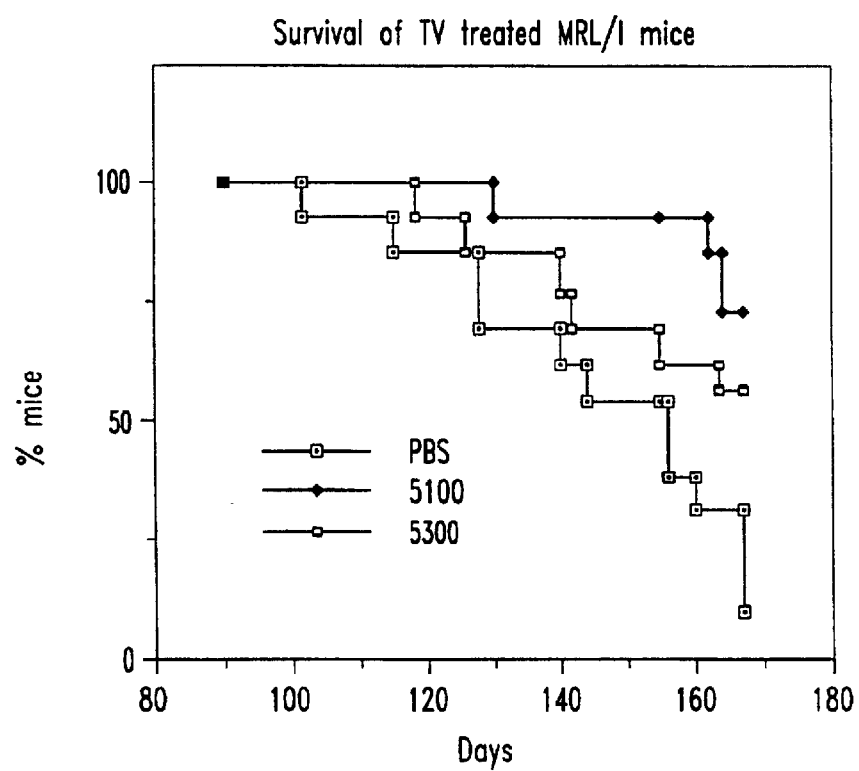
FIG. 9 shows the effect of R38 (also referred to herein as 5100) treatment on prolongation of survival of lupus mice.

The survival of MRL/1pr/1pr mice treated with 5100, 5200 or 5300 was compared to that of PBS treated mice. As shown in FIGS. 8 and 9, the survival of mice treated with 5100 or 5200 was significantly higher than that of control mice. In FIGS. 8 and 9 the time in days shown on the x axis relates to the age of the mice. Two mice in each group were sacrificed after 5 months and their kidneys evaluated by light microscopy. The kidneys from the control mice showed severe diffuse proliferative glomerulonephritis with crescents and sclerosis whereas the 5100 or 5200 treated mice showed mild proliferative changes with no crescents and no sclerosis.

EXAMPLE 5—ANALYSIS OF THE CORRELATION BETWEEN ANTI-R38 ANTIBODIES AND DISEASE ACTIVITY

Urine from lupus patients with and without renal disease in active and inactive state were collected repeatedly and tested for presence of anti-R38 antibodies by ELISA. Activity of the disease was evaluated also be accepted clinical and serological parameters (Lockshin M. D. et al Am. J. Med. (1984) 77 893–898) and their correlation with anti-R38 levels was compared.

103 urine samples of 37 SLE patients were tested for anti-R38 activity by ELISA as described above. 23 samples were from patients without renal disease and 80 samples from patients with renal disease. A further 12 samples from patients with renal disease not relates to SLE were also included The following results were obtained:

| SLE | Present | Present | Absent |
|---|---|---|---|
| Renal Disease | Absent | Present | Present |
| No. Samples | 23 | 80 | 12 |
| Urine anti-R38 O.D. (Mean + S.E.) | 0.035 ± 0.003 | 0.229 ± 0.03* | 0.07 ± 0.01 |

*$p < 0.001$

Positivity of the samples in those patients with renal disease usually correlated with active disease according to an activity score that includes 19 clinical laboratory parameters (Lockshin M. D. et al supra). These parameters included assessment of the presence/absence/condition of the following clinical criteria alopecia, rash, fever, serositis, athralgia/arthritis, mucosal ulcers, neurological events, malaise, fundi changes, nodes, spleen and the following blood tests including ESR (erythrocyte sedimentation rate), anti DNA antibodies, complement (U/ml), creatinine, haemoglobin (g/dl), PLT platelets (/mm$^2$) or urinalysis. The assessment of these parameters is measured as described in Lockshin supra. The overall percentage given reflects only the assessed parameters.

Figure 5:
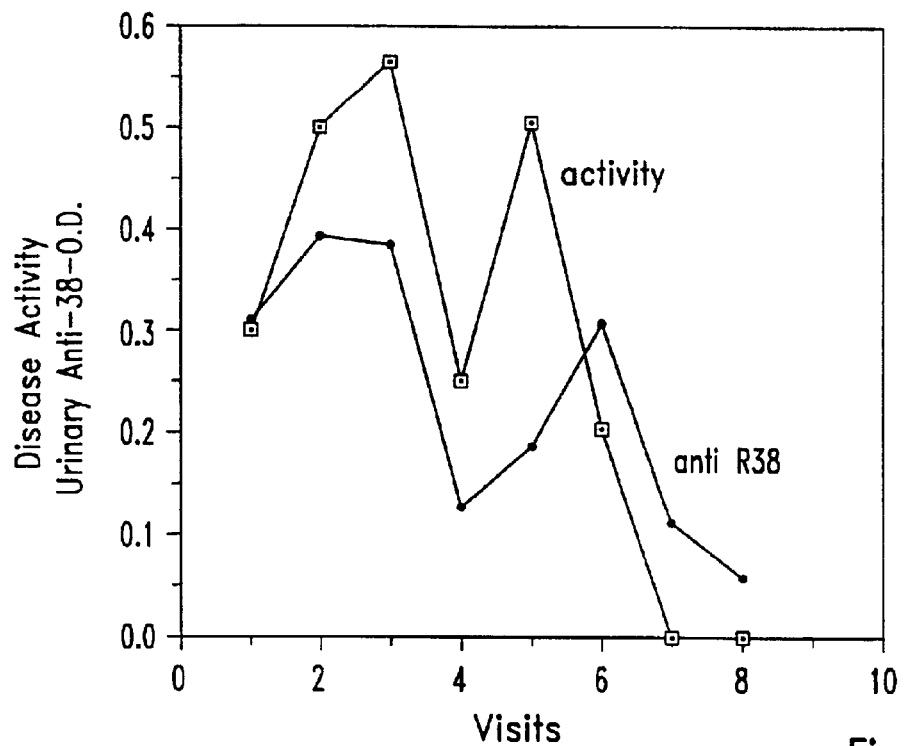
FIGS. 5,6 and 7 show the correlation between lupus activity score and urinary anti-R38 level in three lupus patients.
Figure 6:
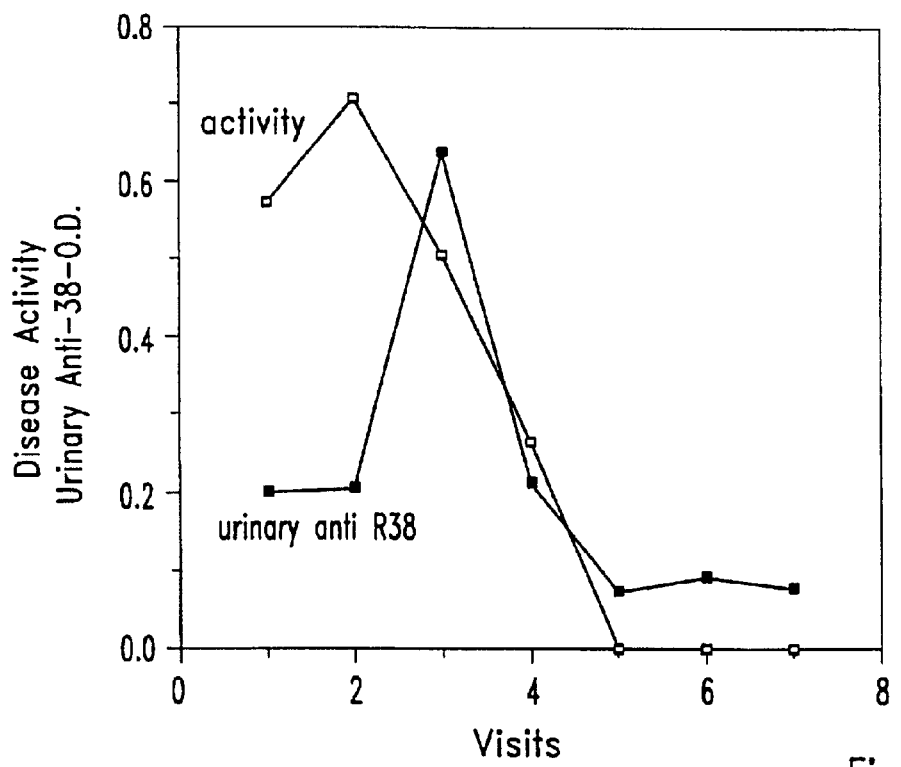
Figure 7:
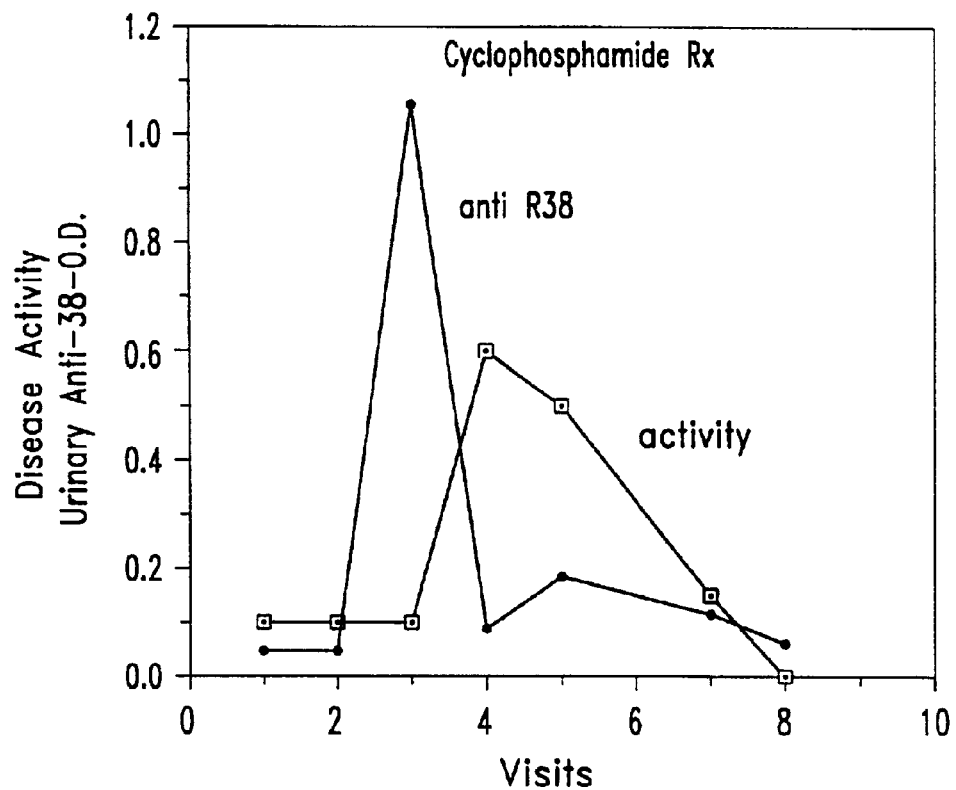

In some patients urine samples were tested in more than one occasion and a good correlation between the clinical activity and the level of anti R38 binding were observed. Three representative examples from three different lupus patients are shown in FIGS. 5,6 and 7 where the x-axis shows the No. of the hospital visit and y-axis, the observed binding (OD at 405 nm) or percentage of the activity score described above. As can be seen from these Figures, the assay using the R38 peptide provides a reliable method of monitoring disease activity.

EXAMPLE 6—ANALYSIS OF THE CORRELATION BETWEEN ANTI-5200 (R38') ANTIBODIES AND DISEASE ACTIVITY

In an additional experiment, 178 urine samples from lupus patients, 24 with and 22 without renal disease in active and inactive state were collected and tested for presence of anti-5200 antibodies by ELISA as described above. The following results were obtained:

| Renal Disease | Absent | Present |
|---|---|---|
| No. Samples | 46 | 132 |
| Urine anti-5200 O.D. (Mean + S.E.) | 0.05 ± 0.005 | 0.335 ± 0.035* |

*p < 0.001

EXAMPLE 7—ANALYSIS OF THE CORRELATION BETWEEN ANTI-5100 (R38) ANTIBODIES AND DISEASE ACTIVITY 45 urine samples from 21 lupus patients, some with and some without renal disease in active and inactive state were collected and tested for presence of anti-5100 antibodies by direct ELISA as described above.

The following results were obtained:

| Renal Disease | Absent | Present |
|---|---|---|
| No. Samples | 6 | 39 |
| Urine anti-5100 O.D. (Mean + S.E.) | 0.058 ± 0.006 | 0.376 ± 0.05* |

*p < 0.03

EXAMPLE 8—ANALYSIS OF THE CORRELATION BETWEEN ANTI-5200 (R38') ANTIBODIES AND DISEASE ACTIVITY 52 urine samples from 21 lupus patients, with and without renal disease in active and inactive state were collected and tested for presence of anti-5200 antibodies by ELISA as described above.

The following results were obtained:

| Renal Disease | Absent | Present |
|---|---|---|
| No. Samples | 6 | 46 |
| Urine anti-5200 O.D. (Mean + S.E.) | 0.052 ± 0.03 | 0.431 ± 0.09 |

EXAMPLE 9—ANALYSIS OF THE CORRELATION BETWEEN ANTI-5108, 5101, 5109 AND 5110—ANTIBODIES AND DISEASE ACTIVITY 24 urine samples from some of the lupus patients of Examples 7 and 8, 2 with and 22 without renal disease in active and inactive state were collected and tested for binding to 5108 peptides by ELISA as described above.

The following results were obtained:

| Renal Disease | Absent | Present |
|---|---|---|
| No. Samples | 2 | 22 |
| Urine anti-5108 O.D. (Mean + S.E.) | 0.064 ± 0.05 | 0.672 ± 0.1 |

Similar results were observed for binding of peptides 5101, 5109 and 5110.

EXAMPLE 10—DIRECT BINDING OF C72 and B3 to R38 AND ANALOG PEPTIDES

The peptides of the present invention were tested for their ability to bind directly with C72 murine anti-DNA antibodies and B3 human anti-DNA antibodies according to the methods described hereinabove. The results of the direct binding study are reported in Table 3:

TABLE 3

Direct Binding Of C72 And B3 To R38 And Analog Peptides

| Peptide # | C72 Binding[†] | B3 Binding[‡] |
|---|---|---|
| 5100 | 2.57 | 0.9 |
| 5200 | 1.6 | 0.25 |
| 5300 | 0.03 | 0.03 |
| 5101 | 1.11 | 0.1 |
| 5102 | 0.1 | 0.02 |
| 5103 | 0.03 | 0.02 |
| 5104 | 0.06 | 0.02 |
| 5105 | 0.07 | 0.02 |
| 5106 | 1.9 | 0.16 |
| 5107 | 0.05 | 0.01 |
| 5108 | 2.75 | 1.93 |
| 5109 | 2.72 | 1.94 |
| 5110 | 2.8 | 1.83 |
| 5111 | 0.01 | 0.01 |
| R18 | 0.01 | NT* |
| R28 | 0.01 | NT |
| R30 | 0.75 | NT |
| R37 | 1.8 | NT |

*NT—Not Tested
[†]- O.D. in a direct binding ELISA test after one (1) hour.
[‡]- O.D. in a direct binding ELISA test after two (2) hours.

EXAMPLE 11: COMPETITIVE INHIBITION OF C72 BINDING TO R38 WITH ANALOG PEPTIDES

A competitive inhibition study compared how each of the peptides competes with R38 (5100) for binding to the C72 anti-DNA antibody. Conducted according to the methods described hereinabove, the results of the study are disclosed in Table 4 below and are further elucidated by reference to FIG. 10.

TABLE 4

Inhibition of C72 Binding to R38

| Peptide # | 50% inhibition of C72 binding to mouse R38 (5100) in µg/ml |
|---|---|
| 5100 | 10 |
| 5200 | 10 |
| 5300 | 85 |
| 5101 | 5 |
| 5102 | 30 |
| 5103 | NI** |
| 5104 | NI |
| 5105 | NI |
| 5106 | 2.5 |
| 5107 | 85 |
| 5108 | 2 |
| 5109 | 0.7 |
| 5110 | 0.7 |
| 5111 | NI |

*Concentration of competitive inhibitor which resulted in 50% inhibition of the binding of C72 anti-DNA antibody to peptide 5100 (R38) in an ELISA test.
**NI—No Inhibition It should be understood that the foregoing description and examples are merely illustrative and that many modifications and variations may be made thereto by one skilled in art without departing from the scope and spirit of the invention as claimed hereinbelow.

What is claimed is:

1. A pharmaceutical composition comprising an effective amount of at least one laminin peptide or fragment thereof selected from the group consisting of 5108 (SEQ ID NO. 19), 5109 (SEQ ID NO. 20), 5110 (SEQ ID NO: 21), 5200 (SEQ ID NO. 10) wherein said fragments retain the activity of the complete peptide and a pharmaceutically acceptable carrier.

2. The pharmaceutical composition according to claim 1, further comprising at least one additional laminin peptide selected from the group consisting of R38 (SEQ ID NO. 9), 5200 (SEQ ID NO. 10), 5108 (SEQ ID NO. 19), 5109 (SEQ ID NO. 20), and 5110 (SEQ ID NO. 21).

3. A peptide selected from the group consisting of peptides having the amino acid sequences:
KEGYKVRLDLNTTLEFRTTSK (SEQ ID NO. 10),
KAGYKVRLALNITLAFRTTSK (SEQ ID NO. 19),
KEGYKVRLALNITLEFRTTSK (SEQ ID NO. 20),
and KEGYKVRLDLNITLAFRTTSK (SEQ ID NO. 21).

4. The pharmaceutical composition according to claim 1, wherein the laminin peptide or fragment thereof has the sequence KAGYKVRLALNITLAFRTTSK (SEQ ID NO. 19).

5. The pharmaceutical composition according to claim 1, wherein the laminin peptide or fragment thereof has the sequence KEGYKVRLALNITLEFRTTSK (SEQ ID NO. 20).

6. The pharmaceutical composition according to claim 1, wherein the laminin peptide or fragment thereof has the sequence KEGYKVRLDLNITLAFRTTSK (SEQ ID NO. 21).

7. The pharmaceutical composition according to claim 1, wherein the laminin peptide or fragment thereof has the sequence KEGYKVRLDLNTTLEFRTTSK (SEQ ID NO. 10).

8. The pharmaceutical composition according to claim 1, further comprising the additional peptide KEGYKVRLDLNITLEFRTTSK (SEQ ID NO. 9).

* * * * *

SEQUENCE LISTING

<160> NUMBER OF SEQ ID NOS: 22

<210> SEQ ID NO 1
<211> LENGTH: 21
<212> TYPE: PRT
<213> ORGANISM: mouse

<400> SEQUENCE: 1

```
Lys Glu Gly Tyr Lys Val Arg Leu Asp Leu Asn Ile Thr Leu Glu Phe
 1               5                  10                  15

Arg Thr Thr Ser Lys
            20
```

<210> SEQ ID NO 2
<211> LENGTH: 22
<212> TYPE: PRT
<213> ORGANISM: mouse

<400> SEQUENCE: 2

```
Arg Pro Val Arg His Ala Gln Cys Arg Val Cys Asp Gly Asn Ser Thr
 1               5                  10                  15

Asn Pro Arg Glu Arg His
            20
```

<210> SEQ ID NO 3
<211> LENGTH: 21
<212> TYPE: PRT
<213> ORGANISM: mouse

<400> SEQUENCE: 3

```
Lys Asn Leu Glu Ile Ser Arg Ser Thr Phe Asp Leu Leu Arg Asn Ser
 1               5                  10                  15

Tyr Gly Val Arg Lys
            20
```

<210> SEQ ID NO 4
<211> LENGTH: 19
<212> TYPE: PRT
<213> ORGANISM: mouse

<400> SEQUENCE: 4

```
Thr Ser Leu Arg Lys Ala Leu Leu His Ala Pro Thr Gly Ser Tyr Ser
 1               5                  10                  15

Asp Gly Gln
```

<210> SEQ ID NO 5
<211> LENGTH: 17
<212> TYPE: PRT
<213> ORGANISM: mouse

<400> SEQUENCE: 5

```
Lys Ala Thr Pro Met Leu Lys Met Arg Thr Ser Phe His Gly Cys Ile
 1               5                  10                  15

Lys
```

<210> SEQ ID NO 6
<211> LENGTH: 17
<212> TYPE: PRT
<213> ORGANISM: mouse

<400> SEQUENCE: 6

Asp Gly Lys Trp His Thr Val Lys Thr Glu Tyr Ile Lys Arg Lys Ala
1               5                   10                  15

Phe

<210> SEQ ID NO 7
<211> LENGTH: 21
<212> TYPE: PRT
<213> ORGANISM: mouse

<400> SEQUENCE: 7

Lys Glu Gly Tyr Lys Val Arg Leu Asp Leu Asn Ile Thr Leu Glu Phe
1               5                   10                  15

Arg Thr Thr Ser Lys
            20

<210> SEQ ID NO 8
<211> LENGTH: 22
<212> TYPE: PRT
<213> ORGANISM: mouse

<400> SEQUENCE: 8

Lys Gln Asn Cys Leu Ser Ser Arg Ala Ser Phe Arg Gly Cys Val Arg
1               5                   10                  15

Asn Leu Arg Leu Ser Arg
            20

<210> SEQ ID NO 9
<211> LENGTH: 21
<212> TYPE: PRT
<213> ORGANISM: mouse

<400> SEQUENCE: 9

Lys Glu Gly Tyr Lys Val Arg Leu Asp Leu Asn Ile Thr Leu Glu Phe
1               5                   10                  15

Arg Thr Thr Ser Lys
            20

<210> SEQ ID NO 10
<211> LENGTH: 21
<212> TYPE: PRT
<213> ORGANISM: mouse

<400> SEQUENCE: 10

Lys Glu Gly Tyr Lys Val Arg Leu Asp Leu Asn Thr Thr Leu Glu Phe
1               5                   10                  15

Arg Thr Thr Ser Lys
            20

<210> SEQ ID NO 11
<211> LENGTH: 21
<212> TYPE: PRT
<213> ORGANISM: Homo sapiens

<400> SEQUENCE: 11

Lys Glu Gly Tyr Lys Val Gln Ser Asp Val Asn Ile Thr Leu Glu Phe
1               5                   10                  15

Arg Thr Ser Ser Gln
            20

<210> SEQ ID NO 12
<211> LENGTH: 16

```
<212> TYPE: PRT
<213> ORGANISM: mouse

<400> SEQUENCE: 12

Lys Glu Gly Tyr Lys Val Arg Leu Asp Leu Asn Ile Thr Leu Glu Phe
 1               5                  10                  15

<210> SEQ ID NO 13
<211> LENGTH: 12
<212> TYPE: PRT
<213> ORGANISM: mouse

<400> SEQUENCE: 13

Val Arg Leu Asp Leu Asn Ile Thr Leu Glu Phe Arg
 1               5                  10

<210> SEQ ID NO 14
<211> LENGTH: 14
<212> TYPE: PRT
<213> ORGANISM: mouse

<400> SEQUENCE: 14

Leu Asp Leu Asn Ile Thr Leu Glu Phe Arg Thr Thr Ser Lys
 1               5                  10

<210> SEQ ID NO 15
<211> LENGTH: 21
<212> TYPE: PRT
<213> ORGANISM: mouse

<400> SEQUENCE: 15

Ala Glu Gly Tyr Ala Val Ala Leu Asp Leu Asn Ile Thr Leu Glu Phe
 1               5                  10                  15

Ala Thr Thr Ser Ala
                20

<210> SEQ ID NO 16
<211> LENGTH: 21
<212> TYPE: PRT
<213> ORGANISM: mouse

<400> SEQUENCE: 16

Lys Glu Gly Tyr Lys Val Glu Leu Asp Leu Asn Ile Thr Leu Glu Phe
 1               5                  10                  15

Glu Thr Thr Ser Lys
                20

<210> SEQ ID NO 17
<211> LENGTH: 21
<212> TYPE: PRT
<213> ORGANISM: mouse

<400> SEQUENCE: 17

Lys Glu Gly Tyr Lys Val Glu Leu Asp Leu Asn Ile Thr Leu Glu Phe
 1               5                  10                  15

Arg Thr Thr Ser Lys
                20

<210> SEQ ID NO 18
<211> LENGTH: 21
<212> TYPE: PRT
<213> ORGANISM: mouse

<400> SEQUENCE: 18
```

```
<210> SEQ ID NO 19
<211> LENGTH: 21
<212> TYPE: PRT
<213> ORGANISM: mouse

<400> SEQUENCE: 19

Lys Ala Gly Tyr Lys Val Arg Leu Ala Leu Asn Ile Thr Leu Ala Phe
 1               5                  10                  15
Arg Thr Thr Ser Lys
            20

<210> SEQ ID NO 20
<211> LENGTH: 21
<212> TYPE: PRT
<213> ORGANISM: mouse

<400> SEQUENCE: 20

Lys Glu Gly Tyr Lys Val Arg Leu Ala Leu Asn Ile Thr Leu Glu Phe
 1               5                  10                  15
Arg Thr Thr Ser Lys
            20

<210> SEQ ID NO 21
<211> LENGTH: 21
<212> TYPE: PRT
<213> ORGANISM: mouse

<400> SEQUENCE: 21

Lys Glu Gly Tyr Lys Val Arg Leu Asp Leu Asn Ile Thr Leu Ala Phe
 1               5                  10                  15
Arg Thr Thr Ser Lys
            20

<210> SEQ ID NO 22
<211> LENGTH: 12
<212> TYPE: PRT
<213> ORGANISM: Homo sapiens

<400> SEQUENCE: 22

Val Gln Ser Asp Val Asn Ile Thr Leu Glu Phe Arg
 1               5                  10
```

Also shown above (SEQ ID NO 18 continuation):
```
Lys Glu Gly Tyr Lys Val Arg Leu Asp Leu Asn Ile Thr Leu Glu Phe
 1               5                  10                  15
Glu Thr Thr Ser Lys
            20
```